United States Patent [19]

Onopchenko et al.

[11] 4,022,838
[45] May 10, 1977

[54] PROCESS FOR PREPARING DIARYLKETONES

[75] Inventors: Anatoli Onopchenko, Monroeville; Johann G. D. Schulz, Pittsburgh, both of Pa.

[73] Assignee: Gulf Research & Development Company, Pittsburgh, Pa.

[22] Filed: May 27, 1975

[21] Appl. No.: 581,287

[52] U.S. Cl. .......................... 260/591; 260/590 D; 260/568; 260/517; 260/511
[51] Int. Cl.$^2$ ........................................ C07C 49/76
[58] Field of Search ................................. 260/591

[56] References Cited
UNITED STATES PATENTS 3,479,400  11/1969  Lese et al. ............................ 260/591
3,641,132  2/1972  Schulz et al. ........................ 260/591

FOREIGN PATENTS OR APPLICATIONS 703,012  2/1965  Canada .............................. 260/591
934,525  9/1955  Germany ........................... 260/591

OTHER PUBLICATIONS

Bengtsson, *Acta Chem Scan*, vol. 9(1), pp. 177–178 (1955).
Ogato et al, *Tetrahedron*, vol. 25, pp. 4919–4922 (1969).
Ogato et al, *J. Org. Chem*, vol. 34(4), pp. 845–847 (1969).
Akaboyashi, *Yuki Gasil Kogaku* Kygkai-shi vol. 27, pp. 233–242 (1969).

*Primary Examiner*—James O. Thomas, Jr.
*Assistant Examiner*—James H. Reamer

[57] ABSTRACT

A process for converting a 1,1-diarylalkane, such as a 1,1-bis(alkylphenyl)alkane, to the corresponding diarylketone which involves oxidizing the 1,1-diarylalkane using critical amounts of 1,1-diarylalkane, nitric acid and water. In a preferred embodiment the reaction product obtained as a result of the oxidation of a 1,1-bis(alkylphenyl)alkane is then further subjected to reaction with additional nitric acid at elevated temperatures in a second stage to convert each of the nuclear alkyl groups on the alkyl-aromatic charge to carboxyl groups and the dilute nitric acid remaining is employed in the first stage as oxidant.

9 Claims, 1 Drawing Figure

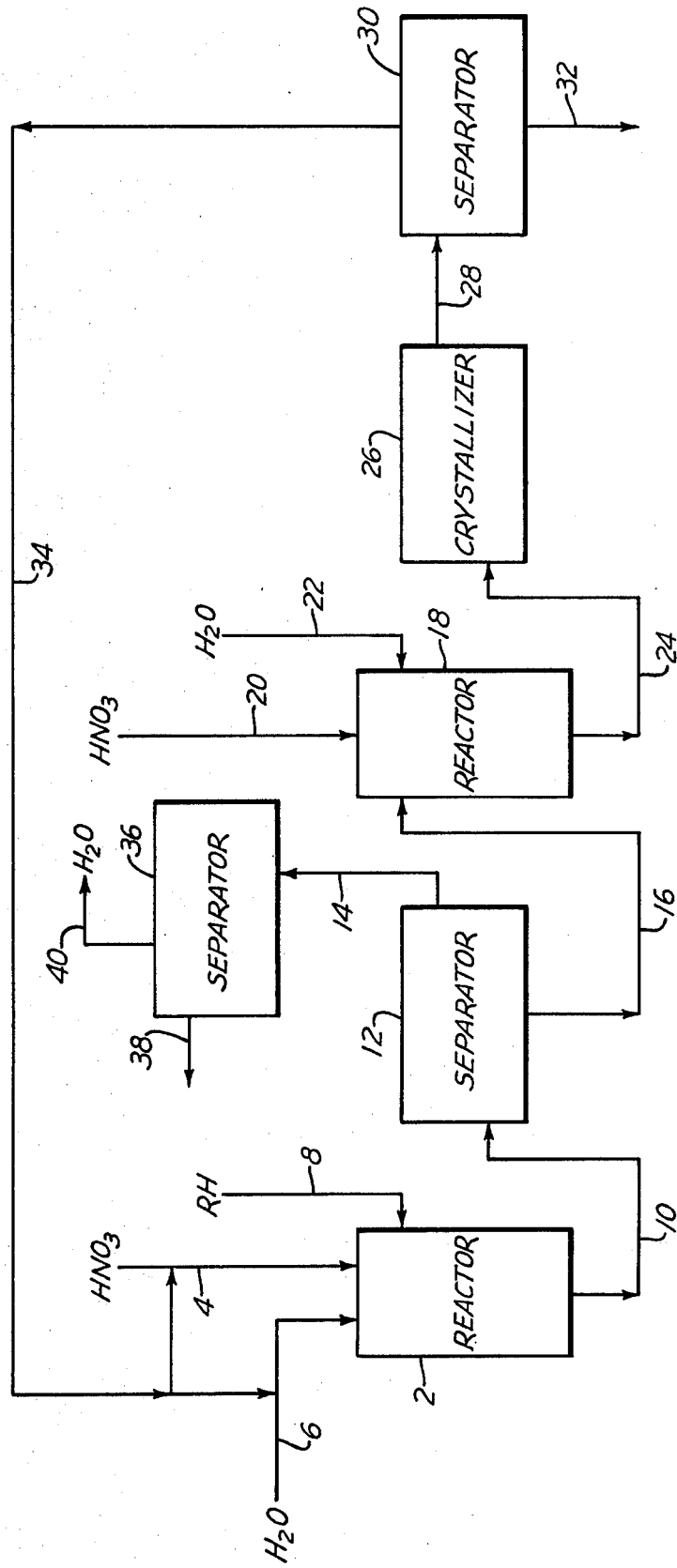

PROCESS FOR PREPARING DIARYLKETONES

BACKGROUND OF THE INVENTION

1. Field of the Invention

The invention defined herein relates to the conversion of a 1,1-diarylalkane to the corresponding diarylketone without appreciably converting any nuclear alkyl substituents that may be present on the aryl portion thereof. The invention also relates to the further conversion of the alkyl substituents with concentrated nitric acid and to procedures wherein substantially all of the nitric acid employed in the process is utilized.

2. Description of the Prior Art

U.S. Pat. No. 3,075,007 to McCracken et al discloses a process wherein a diarylalkane is subjected to oxidation with nitric acid to obtain a diarylketone, particularly a diarylketone polycarboxylic acid. U.S. Pat. No. 3,479,400 to Lese et al. discloses a process wherein a diarylalkane is subjected to oxidation with nitric acid in a first stage to obtain oxidation products of the diarylalkane, the oxidation products so obtained are further subjected to oxidation with additional nitric acid to obtain a diarylketone carboxylic acid and using the residual nitric acid effluent for the initial oxidation. In U.S. Pat. No. 3,641,132 to Schulz et al, nitric acid is added to a diarylalkane to obtain a nitro benzophenone.

SUMMARY OF THE INVENTION

The process defined and claimed herein relates to the oxidation of a 1,1-diarylalkane using critical amounts of 1,1-diarylalkane, nitric acid and water to obtain the corresponding diarylketones without appreciable oxidation of any nuclear alkyl substituents that may be present on the aryl portion thereof. In a preferred embodiment the process relates to a process wherein a 1,1-bis(alkylphenyl)alkane is subjected to nitric acid treatment in a first stage, as defined above, the resulting product is then subjected to oxidation with concentrated nitric acid at an elevated temperature in a second stage to oxidize the alkyl substituents to carboxyl groups to obtain the corresponding diarylketone carboxylic acid and the residual nitric acid is employed as oxidant in the first stage.

BRIEF DESCRIPTION OF THE DRAWING AND PROCESS

The drawing is a flow diagram describing the process defined and claimed herein. Into a stirred reactor 2 there is introduced nitric acid by line 4, water by line 6 and a 1,1-diarylalkane by line 8. If desired two or more of lines 4, 6, and 8 can be combined before introduction into reactor 2. The 1,1-diarylalkane can be represented by the following structural formula:

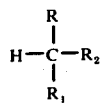

wherein R and $R_1$, the same or different, are aryl radicals containing one or more rings, at least one of which is an aromatic ring, such as phenyl, biphenyl, naphthyl, phenanthryl, anthryl, indyl, dihydronaphthyl, cyclohexylphenyl, etc., but which is preferably a phenyl radical; said aryl radicals preferably carrying from one to two alkyl substituents thereon, each alkyl substituent having from one to four carbon atoms, preferably from one to two carbon atoms; and $R_2$ being an alkyl radical having from one to 16 carbon atoms, preferably one. Specific examples of diarylalkanes that can be employed herein are the following:

1,1-bis(p-tolyl)ethane
1,1-bis(p-tolyl)propane
1,1-bis(p-tolyl)butane
1,1-bis(p-tolyl)hexane
1,1-bis(p-tolyl)octane
1,1-bis(p-tolyl)decane
1,1-bis(p-tolyl)dodecane
1,1-bis(p-tolyl)tetradecane
1,1-bis(p-tolyl)hexadecane
1,1-bis(4-ethylphenyl)ethane
1,1-bis(4-octylphenyl)pentane
1,1-bis(4-decylphenyl)octane
1,1-bis(4-hexadecylphenyl)hexadecane
1,1-bis(3,4-dimethylphenyl)ethane
1,1-bis(3,4-dimethylphenyl)propane
1,1-bis(3,4-dimethylphenyl)butane
1,1-bis(3,4-dimethylphenyl)hexane
1,1-bis(3,4-dimethylphenyl)octane
1,1-bis(3,4-dimethylphenyl)decane
1,1-bis(3,4-dimethylphenyl)dodecane
1,1-bis(3,4-dimethylphenyl)tetradecane
1,1-bis(3,4-dimethylphenyl)hexadecane
1,1-bis(3,4-diethylphenyl)ethane
1,1-bis(3,4-octylphenyl)pentane
1,1-bis(3,4-decylphenyl)octane
1,1-bis(3,4-hexadecylphenyl)hexadecane
1,1-bis(2,2'-dibromo,3,4,3'4'-tetramethylphenyl)ethane
1-(3-methyl,4-ethylphenyl),1-(2'-nitro,3',4'-diethylphenyl)ethane
1,1-bis(3,4,3',4'-tetramethyl,5-aminophenyl)ethane
1-(3,4-diethylphenyl),1-(3',4'-diisopropylphenyl)ethane
1-(2-methyl-4,isopropylphenyl),1-(4-methyl-2-nitrophenyl)ethane
1,1-bis(3-ethyl,4-butylphenyl)isobutane
1-(4-propylphenyl),1-(2-ethylphenyl)octane
1,1-bis(2,4-diisopropylphenyl)hexadecane
1,1-bis(2-ethyl,4-butylphenyl)isobutane
1,1-bis(2-ethylphenyl)ethane
1-(4-propylphenyl),1-(4-methylphenyl)propane
1-(2,4-dimethylphenyl)-1-(4-propylphenyl)pentane
1,1-bis(2-methylanthryl)butane
1-(2-methyl,4-chlorophenyl),1-(2-ethylphenyl)octane
1,1-bis(tetramethylphenyl)decane
1-(2-methyl,4-isopropylphenyl),1-(4-methyl-2-nitrophenyl)ethane
1,1-bis(2-hexylphenanthryl),3,3-dimethylpentane
1-(2-propyl,3-carboxynaphthyl),1-(4-butylphenyl)hexane
1-(5-octyl,1,4-dihydronaphthyl),1-(2-methylnaphthyl)dodecane
1-(bromo-9,10-dihydrophenanthryl),1-(2-ethylphenyl)decane
1-(2-propyl,3-aminophenyl),1-(4-methyl-2-sulfophenyl)ethane, etc.

The preferred diarylalkanes that will be oxidized herein are 1,1-bis(p-tolyl)ethane and 1,1-bis(3,4-dimethylphenyl)ethane. The amount of nitric acid and water introduced into reactor 2 by lines 4 and 6, respectively can be varied over a wide range but are so correlated that the resultant total amounts of each will result in an aqueous nitric acid solution having a concentration of about one to about 40 weight percent or higher, preferably about two to about 35 weight percent. The molar amount of nitric acid employed, determined as 100 percent nitric acid, relative to the mols of diarylalkane must be in the range of about 0.1:1 to about 8:1, preferably about 1.5:1 to about 6:1. In order to assure that a diarylketone will be obtained, however, and that no appreciable oxidation of any nuclear alkyl substituents to carboxyl groups takes place in reactor 2, it is critical that the relative amounts of diarylalkane, nitric acid and water introduced therein be within well-defined limits. These limits can be determined by multiplying the ratio of the absolute mols of nitric acid to the mols of diarylalkane times the concentration of the nitric acid in weight percent:

$$\text{Nitric Acid Parameter} = \left(\frac{\text{Concentration of HNO}_3}{\text{in Weight Percent}}\right)\left(\frac{\text{Mols of HNO}_3}{\text{Mols of Diarylalkane}}\right)$$

we have found that when the numerical product of the above is in the range of about 1.0 to 150, preferably about 5 to about 75, the primary product is a diarylketone and when the diarylalkane carries nuclear alkyl substituents thereon, no appreciable conversion thereof to carboxyl groups takes place. As shown in our copending application Ser. No. 581,087, filed concurrently herewith, when the product of the above is in excess of 150, the amount of diarylketone is substantially reduced and a substantial amount of a 1,1-diaryl-2,2-dinitrolethylene is obtained instead. As a matter of convenience we have termed these limits as "nitric acid parameters." The temperature in reactor 2 can be in the range of about 30° to about 200° C., preferably about 60° to about 150° C., the pressure about atmospheric to about 500 pounds per square inch gauge (about atmospheric to about 35 kilograms per square centimeter), preferably about atmospheric to about 100 pounds per square inch gauge (about atmospheric to about 7 kilograms per square centimeter), and a residence time of about one minute to about 24 hours, preferably about 5 minutes to about 4 hours.

The reaction product obtained can then be passed to a separator 12 by line 10 wherein the organic phase and the aqueous phase can be separated from each other by any convenient or suitable means, for example, by decantation or filtration. The aqueous phase can be removed from separator 12 by line 14 and the organic phase by line 16.

The organic phase may contain some unreated diarylalkane and, on a diarylalkane-free basis, from about 60 to about 90 weight percent of the desired diarylketone, from about five to about 30 weight percent of a 1,1-diaryl-2-nitroethylene and from about 5 to about 10 weight percent of other oxidation products.

The desired diarylketone can be recovered from the organic phase in any convenient manner. Thus, if the reaction in reactor 2 has been carried out at a temperature above about 140° C., the organic phase will be a solid. Recovery of the desired diarylketone can be effected by dissolving the organic phase in a solvent, such as ethanol, at room temperature or up to the boiling point of the solvent and then allowing crystallization to occur. If the reaction has been carried out at a temperature below about 140° C. the organic phase will be a viscous liquid. Recovery of diarylketone from the latter can be carried out by dissolving it in a solvent, such as methanol, followed by treatment with a base, such as sodium hydroxide, to precipitate the diarylketone, which then is recovered by filtration. This recovery procedure is described in more detail in our copending application Ser. No. 581,288, filed concurrently herewith. Diarylketones that can be obtained include, preferably, 4,4'-dimethylbenzophenone and 3,4,3',4'-tetramethylbenzophenone. The fact that the organic phase is a viscous liquid when the reaction is carried out at a temperature below about 140° C. is surprising and such discovery facilitates the operation of our preferred embodiment. We expected the diarylketone to be a solid, because it is known in the literature, that 3,4,3',4'-tetramethylbenzophenone has a melting point of 140° C. Accordingly, when in our preferred embodiment the organic phase in line 16 is transferred to reactor 18, the fact that it is a liquid facilitates its transfer thereto and its subsequent reaction therein.

Accordingly, in our preferred embodiment there is also introduced into stirred reactor 18 nitric acid by line 20 and water by line 22. If desired lines 20 and 22 can be combined prior to introduction into reactor 18. The aqueous concentration of the nitric acid in the reactor, on the basis of the total amount of nitric acid and water introduced therein, is about five to about 50 weight percent, preferably about 10 to about 30 weight percent. In the preferred embodiment, the diarylketone will be one carrying nuclear alkyl groups thereon. The amount of nitric acid, defined as 100 percent nitric acid, needed in reactor 18, will depend on the number of alkyl groups to be oxidized, and, in general, will amount to about 2 to about 6 mols of nitric acid, preferably about 2 to about 4 mols of nitric acid, per alkyl substituent. The temperature in reactor 18 will be in the range of about 150° to about 200° C., preferably about 160° to about 180° C., the pressure about 100 to about 600 pounds per square inch gauge (about 7 to about 42 kilograms per square centimeter), preferably about 150 to about 400 pounds per square inch gauge (about 10 to about 28 kilograms per square centimeter), and the reaction time about 10 minutes to about 12 hours, preferably about 15 minutes to about 3 hours.

The reaction product in reactor 18 is removed therefrom by line 24 and passed to crystallizer 26, which can be maintained at a temperature of about 0° to about 45° C., to crystallize out the desired diarylketone carboxylic acids. The resultant product is transferred by line 28 to separator 30, wherein the desired diarylketone carboxylic acids are removed therefrom by line 32. Diarylketone carboxylic acids that can be obtained include 4,4'-benzophenone dicarboxylic acid and 3,4,3',4'-benzophenone tetracarboxylic acid.

The aqueous layer will contain nitric acid and some small amounts of diarylketone carboxylic acids and precursors thereof. The nitric acid concentration will be low, that is, about 1 to about 25 weight percent, preferably about 4 to about 15 weight percent, corresponding to the concentration desired for utilization in reactor 2. Accordingly, in this specific embodiment, the aqueous phase is removed from separator 30 by line 34 and recycled to line 4 or line 6 or both for use in reactor 2. In a particularly preferred embodiment, the sole charge to the reactor 2 can be, except for makeup, the recycle aqueous phase in line 34 and the diarylalkane in line 8. The subsequent operation of the process remains as defined above.

Preferably, however, the aqueous phase in line 14, which contains little or no nitric acid, some small amounts of diarylketone carboxylic acid and precursors thereof is passed to a separator 36 wherein the aqueous phase is extracted with a solvent, such as ethyl acetate, to remove the acidic components therefrom. The latter products can be removed from the system by line 38 and recovered as additional product. The water, substantially free of chemical product, can be removed from the system by line 40 and discarded as waste without causing appreciable ecological problems.

Thus the system defined herein can be used to produce diarylketones without oxidation of nuclear alkyl substituents that may be present. In a preferred embodiment diarylketone carboxylic acids can be obtained easily by further oxidation of the diarylketones so obtained and the same oxidant, $HNO_3$, used to produce the diarylketones can be used to produce the diarylketone carboxylic acids. In an especially preferred embodiment, the oxidant remaining in the second stage can be used in the first stage and since all of the oxidant can be consumed in the two stages, disposal problems for waste oxidant are eliminated and the economic aspects of the processes are greatly improved.

DESCRIPTION OF PREFERRED EMBODIMENTS

EXAMPLE I

A 700 milliliter, 304-stainless steel magnetically-stirred autoclave equipped with a heating mantle and cooling coils was charged with 140 grams (0.59 mol) of 1,1-bis(3,4-dimethylphenyl)ethane (DXE) and 70 grams of water and then heated to a temperature of 100° C., developing a pressure of 17 pounds per square inch gauge (1.2 kilograms per square centimeter). While maintaining this temperature, a mixture of 100 grams of 70 percent aqueous nitric acid and 150 grams of water were additionally added to the autoclave over a period of 1.75 hours. The concentration of the nitric acid in the autoclave, based on the total amount of water and nitric acid added thereto, was therefore 21 percent and the absolute amount of nitric acid was 1.12 mols, resulting in a molar nitric acid to DXE ratio of 1.9. The nitric acid parameter was therefore $$21 \times \frac{1.12}{0.59}$$

or 39.9. The reaction was continued for an additional hour at 100° C., resulting in a final pressure of about 186 pounds per square inch gauge (13 kilograms per square centimeter). The reactor was cooled to room temperature, depressured and a viscous liquid organic material was separated from the aqueous portion by decantation. A small amount of acetone was used to recover organic product adhering to the sides of the autoclave. This was combined with the organic material and the resultant mixture was heated to 100° C. to remove acetone therefrom, leaving behind 172.4 grams of organic material which was analyzed by chromatography. On a DXE-free basis the following selectives were recorded: 72.2 weight percent to 3,4,3',4'-tetramethylbenzophenone (TMB), 20 weight percent to 1,1-bis(3,4-dimethylphenyl)-2-nitroethylene (monoitroethylene), 1.3 weight percent to 1,1-bis (3,4-dimethylphenyl)-2,2-dinitroethylene (dinitroethylene) and 6.5 weight percent to unidentified components. Conversion of DXE in this run was 80 weight percent.

Several additional runs were carried out in the manner of Example I. The data obtained are recorded below in Table I. In Examples II, III, IV and V the product after analysis was further treated to determine whether or not any acidic components were present. This was done by extracting with 10 percent aqueous sodium hydroxide, separating the aqueous phase and adding to it sufficient amounts of aqueous HC1 to neturalize and thereby obtain the acidic material. In Example VIII, the charge was 1,1-bis(para-tolyl)ethane. In Examples VII and VIII the crude reaction product after analysis was combined with 400 milliliters of n-hexane and then filtered to remove small amounts of unreacted DXE and DTE, respectively. The product was then recrystallized from methanol to give TMB and dimethylbenzophenone (DMB) of high purity (98+ percent).

TABLE I

| Example No. | I | II | III | IV | V | VI | VII | VIII |
|---|---|---|---|---|---|---|---|---|
| Autoclave Charge, Grams | | | | | | | | |
| 1,1-bis(3,4-dimethyl-phenyl) ethane (DXE) | 140 | 140 | 140 | 112 | 56 | 140 | 90 | 140** |
| Water | 70 | 70 | 52.5 | 42 | 100 | 35 | 165 | 70 |
| Added via pumping: | | | | | | | | |
| 70 percent $HNO_3$ | 100 | 75 | 75 | 130 | 130 | 50 | 85 | 115 |
| Water | 150 | 150 | 112.5 | 225 | 167 | 75 | — | 150 |
| $HNO_3$/DXE molar ratio | 1.9 | 1.9 | 1.4 | 3.1 | 6.1 | 0.9 | 2.5 | 1.9 |
| $HNO_3$ concentration, weight percent | 21 | 21 | 22 | 23 | 22 | 22 | 24 | 24 |
| Effective nitric acid parameter = $\left(\text{Concentration, }HNO_3\right)\left(\frac{\text{Mols }HNO_3}{\text{Mols DXE}}\right)$ | 39.9 | 39.9 | 30.8 | 71.3 | 134 | 19.8 | 60 | 45.6 |
| Reaction Conditions | | | | | | | | |
| Temperature ° C. | 100 | 103 | 115* | 114 | 108 | 112* | 140* | 108 |
| Final pressure, pounds per square inch gauge (kilograms per square centimeter) | 186 (—) | 195 (—) | 186 (—) | 200 (—) | 177 (—) | 125 (—) | 330 (—) | 270 (—) |
| Run time, hours | 1 | 1 | 1 | 1 | 1 | 1 | 1 | 1 |
| Pump time, hours | 1.75 | 1.25 | 0.8 | 1.2 | 1 | 0.6 | 1 | 1 |
| Selectivity, weight percent (DXE-free basis) | | | | | | | | |
| 3,3',4,4'-tetramethyl-benzophenone | 73.2 | 70.8 | 80.7 | 69 | 54.1 | 68.5 | 79.5 | 70.0 |
| mononitroethylene | 19.6 | 17.8 | 13.1 | 16.7 | 17.9 | 13.4 | 13.6 | — |
| dinitroethylene | 0.9 | 3.0 | — | 2.3 | 15.9 | — | — | — |
| miscellaneous | | | | | | | | |

TABLE I-continued

| Example No. | I | II | III | IV | V | VI | VII | VIII |
|---|---|---|---|---|---|---|---|---|
| (unidentified) | 6.3 | 8.4 | 6.2 | 12.0 | 12.1 | 18.1 | 6.9 | 30 |
| Organic acids recovered, grams | *** | 12.0 | 3.3 | 20.0 | *** | Nil | *** | *** |

*Autoclave temperature raised to 150° C. for about 30 minutes.
**1,1-bis(4-methylphenyl)ethane, 87 percent of which was the p,p' isomer.
***Not determined.

An additional series of runs was carried out in the same autoclave as above. All of the reactants were added at once and slowly heated to 90° C. while stirring and then allowed to react under reflux (100° C.) for about 4 hours. The viscous organic liquid which was obtained was permitted to cool overnight and settle as a bottom layer. The recovered organic product was taken up in acetone, dried over anhydrous magnesium sulfate, filtered, evaporated to dryness and then subjected to analysis by chromatography. The results obtained are summarized below in Table II.

TABLE II

| Example No. | IX | X | XI | XII | XIII |
|---|---|---|---|---|---|
| Autoclave Charge, Grams | | | | | |
| 1,1-bis(3,4-dimethylphenyl)ethane (DXE) | 140 | 140 | 70 | 70 | 140 |
| Water | 165 | 330 | 350 | 330 | 330 |
| 70 percent HNO₃ | 75 | 75 | 37.5 | 75 | 75 |
| HNO₃/DXE molar ratio | 1.4 | 1.4 | 1.4 | 2.8 | 1.4 |
| HNO₃ concentration, weight percent | 22 | 13 | 6.8 | 13 | 13 |
| Effective nitric acid parameter | 30.8 | 18.2 | 9.5 | 36.4 | 18.2 |
| Reaction Conditions | | | | | |
| Temperature, ° C. | 100 | 100 | 100 | 100 | 100 |
| Pressure | atmospheric | atmospheric | atmospheric | atmospheric | atmospheric |
| Reaction time, hours | 4 | 4 | 4 | 4 | 4 |
| Selectivity, weight percent (DXE-free basis) | | | | | |
| 3,4,3',4'-tetramethylbenzophenone | 82 | 87 | 98.7 | 73.3 | 86.9 |
| mononitroethylene | 15.0 | 11.3 | 0.4 | 21.3 | 10.1 |
| dinitroethylene | — | — | — | — | — |
| miscellaneous (unidentified) | 3.0 | 1.7 | 0.9 | 5.4 | 3.0 |

Although excellent results were obtained in Examples I to VIII, it can be seen from the above that selectivities to the desired diarylketone are even greater when all of the reactants are present initially in the reaction zone. As Example XI shows, as the effective nitric acid parameter becomes lower essentially quantitative yields of diarylketone are obtained.

EXAMPLE XIV

Into a 1000 milliliter reaction flask there was placed 40 grams (0.168 mol) of DXE, 330 grams of water and 63 grams (0.7 mol) of 70 percent aqueous nitric acid. The resultant concentration of the nitric acid was thus 10.7 percent, the molar ratio of nitric acid to DXE was 4.0 and the effective nitric acid parameter was 42.8. The reaction mixture was vigorously stirred for 3.5 hours at 100° C. At the end of the reaction period the liquid organic product had settled to the bottom of the flask, and the aqueous filtrate was readily separated therefrom by decantation. The liquid organic product, analyzed by chromatography, containing 2.1 weight percent DXE, 77.4 weight percent TMB, 13.7 weight percent mononitroethylene and 6.8 of unidentified material was transferred to a 700 milliliter, 304 stainless steel, magnetically-stirred autoclave containing 200 grams of water and the temperature was raised to 135° C. while simultaneously adding thereto 129 milliliters of 70 percent aqueous nitric acid over a period of 25 minutes. After addition of nitric acid, the autoclave temperature was raised to 175° C. and maintained at such temperature for 1.5 hours. The autoclave was cooled to room temperature, depressured and the filtrate evaporated to dryness. The residue was dried over the weekend in a vacuum oven and amounted to 45.1 grams. Upon analysis by chromatography slightly more than 95 weight percent thereof was found to be 3,4,3',-4'-tetracarboxybenzophenone (BTA), the remainder being trimellitic acid. The yield of BTA was 84.1 weight percent.

EXAMPLE XV

In this example, spent nitric acid from an operation wherein DXE was oxidized with concentrated nitric acid to obtain BTA was employed as oxidant for converting DXE to the corresponding diarylketone (TMB). Thus, 1.9 mols of DXE and 26.6 mols of 50 percent aqueous nitric acid were stirred and heated at a temperature of 175° C. and a pressure of 200 pounds per square inch gauge (14 kilograms per square centimeter) for 3 hours. The reaction product was cooled to 10° C. to crystallize BTA and then filtered. A portion of this filtrate, designated "spent nitric acid" was evaporated to dryness, producing 8.9 weight percent of solids containing 7.4 weight percent phthalic acid, 35.3 weight percent trimellitic acid, 31.5 weight percent tricarboxylic acids, 20.7 weight percent of BTA, and 5.2 weight percent of unidentified acids. The concentration of the nitric acid in the filtrate was 6.9 weight percent.

Into a glass flask there was placed 250 grams (1.06 mols) of DXE and 1,000 grams of the "spent nitric acid" identified above. The effective nitric acid parameter was $$\left(6.9 \times \frac{69/63}{250/238}\right)$$

or 7.4. The contents of the autoclave were vigorously stirred for 6 hours at 100° C. and atmospheric pressure until brown fumes were no longer given off. The reaction mixture was cooled to room temperature, allowing the heavier liquid organic phase to settle to the bottom of the flask, and the aqueous phase was decanted. Upon evaporation to dryness the aqueous phase produced 72 grams of yellow solids and 902 grams of aqueous condensate. Analysis of the solids by chromatography showed the following composition: 5.4 weight percent phthalic acid, 30.0 weight percent trimellitic acid, 30.6 weight percent tricarboxylic acids, 25.6 weight percent BTA and 5.5 weight percent unidentified material. The condensate was found to contain less than 0.8 weight percent nitric acid. The liquid organic phase was also analyzed by chromatography and was shown to contain 30.8 weight percent of unreacted DXE, 46.8 weight percent TMB, 17.8 weight percent mononitroethylene and 4.6 weight percent unidentified material. The organic phase was taken up with 200 milliliters of methanol, treated dropwise with 10 percent aqueous sodium hydroxide until the solution was just basic resulting in the formation of solids. Filtration, followed by washing with water, and drying in a vacuum oven overnight at 100° C. resulted in 105 grams of pale yellow solids, analyzing 98.6 weight percent TMB. The filtrate was taken to dryness and then extracted with normal hexane, which upon evaporation resulted in 136.2 grams of material composed of 55.3 weight percent DXE, 28.9 weight percent mononitroethylene, 10.1 weight percent TMB and 5.7 weight percent unidentified materials.

EXAMPLE XVI

Into a glass flask there was placed 100 grams (0.42 mol) of DXE and 1,000 grams of spent nitric acid similar to that used in Example XV. Thus the effective nitric acid parameter was $$\left( 6.9 \times \frac{69/63}{100/238} \right)$$

or 18.5. The mixture was stirred vigorously for 3 hours at 100° C. and atmospheric pressure. A liquid organic layer was obtained which was analyzed by chromatography to contain 25.5 weight percent DXE, 53.7 weight percent TMB, 17.1 weight percent mononitroethylene and 3.7 weight percent unidentified compounds. The reaction was continued for an additional 6 hours, the reaction mixture was cooled to atmospheric temperature and the aqueous layer was decanted. Analysis by chromatography of the liquid organic product showed it to contain 5.1 weight percent DXE, 59.8 weight percent TMB, 31 weight percent mononitroethylene and 4.1 weight percent unidentified product. The organic phase was dissolved in 200 milliliters of acetone and then sufficient 10 percent aqueous sodium hydroxide was added thereto until solids formed. Sufficient hydrochloric acid was then added to remove the discoloration that formed. The solid product that formed was filtered, washed twice with water and then dried in a vacuum oven at 100° C. for 6 hours to give 50.7 grams of a pale yellow product that was shown to be 97.8 weight percent TMB. The filtrate from the treatment with sodium hydroxide was evaporated to dryness in a rotary evaporator and extracted with 500 milliliters of acetone. On evaporation of acetone, 58.8 grams of organic products were recovered and analyzed by chromatography to contain 10.4 weight percent DXE, 19.4 weight percent TMB, 52.3 weight percent mononitroethylene and 17.9 weight percent BTA precursors, each of which is suitable as charge for further oxidation with $HNO_3$, as defined herein, to BTA. The filtrate initially decanted was also evaporated to dryness, resulting in 79.1 grams of yellow solids analyzing by chromatography to be 6.6 weight percent phthalic acid, 27.0 weight percent trimellitic acid, 31.0 weight percent tricarboxylic acids of TMB, 32.0 weight percent BTA and 3.3 weight percent unidentified product. The aqueous condensate from the latter contained less than 0.7 weight percent $HNO_3$. Efficiency to TMB in this run was 63 weight percent.

Obviously, many modifications and variations of the invention, as hereinabove set forth, can be made without departing from the spirit and scope thereof, and therefore only such limitations should be imposed as are indicated in the appended claims.

We claim:

1. A process for converting a 1,1-diarylalkane selected from the group consisting of 1,1-di(para-tdyl) ethane and 1,1-bis(3,4-dimethylphenyl) ethane

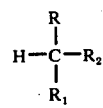

to the corresponding diarylketone without appreciably converting the alkyl substituents on the aryl radicals which comprises heating a mixture of said 1,1-diarylalkane, nitric acid and water, the nitric acid having a concentration of about 1 to about 40 percent, the molar amount of nitric acid determined as 100 percent nitric acid, relative to the molar amount of said 1,1-diarylalkane being in the range of about 1.5:1 to about 6:1, wherein the numerical product obtained by multiplying the concentration of nitric acid in said mixture with the ratio of the absolute mols of nitric acid to the mols of said 1,1-diarylalkane in said mixture is in the range of about 1.0 to 150, at a temperature of about 60° to about 200° C. for about 5 minutes to about 24 hours, to obtain a reaction product containing an organic phase and an aqueous phase, separating said phases from each other, and then recovering said desired 1,1-diarylketone from said organic phase.

2. The process of claim 1 wherein said numerical product is in the range of about 5 to about 75.

3. The process of claim 2 wherein said mixture is heated to a temperature of about 60° to about 150° C. for about 5 minutes to about 4 hours.

4. The process of claim 1 wherein the molar amount of nitric acid determined as 100 percent nitric acid, relative to the molar amount of said 1,1-diarylalkane, is within the range of about 1.5:1 to about 6:1.

5. The process of claim 1 wherein said 1,1-diarylalkane is 1,1-di(para-tolyl)ethane.

6. The process of claim 1 wherein said 1,1-diarylalkane is 1,1-bis(3,4-dimethylphenyl)ethane.

7. The process of claim 1 wherein recovery of 1,1-diarylketone from said organic phase is effected by dissolving said organic phase in a solvent and then recovering said 1,1-diarylketone by recrystallization from said solvent.

8. The process of claim 7 wherein said solvent is methanol.

9. The process of claim 7 wherein said solvent is acetone.

* * * * *